United States Patent
Nakano et al.

(10) Patent No.: US 10,688,030 B2
(45) Date of Patent: Jun. 23, 2020

(54) HAIR CARE COMPOSITION

(71) Applicant: SYMRISE AG, Holzminden (DE)

(72) Inventors: Adelino Nakano, Indaiatuba (BR); Carolina Lourenco, Cotia (BR)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 16/302,881

(22) PCT Filed: Sep. 23, 2016

(86) PCT No.: PCT/EP2016/072776
§ 371 (c)(1),
(2) Date: Nov. 19, 2018

(87) PCT Pub. No.: WO2017/202477
PCT Pub. Date: Nov. 30, 2017

(65) Prior Publication Data
US 2019/0201305 A1 Jul. 4, 2019

(30) Foreign Application Priority Data

May 23, 2016 (WO) ................. PCT/EP2016/061545

(51) Int. Cl.
| | | |
|---|---|---|
| *A61K 8/44* | (2006.01) | |
| *A61Q 5/00* | (2006.01) | |
| *A61K 8/34* | (2006.01) | |
| *A61K 8/37* | (2006.01) | |
| *A61K 8/64* | (2006.01) | |
| *A61K 8/65* | (2006.01) | |
| *A61K 8/97* | (2017.01) | |

(52) U.S. Cl.
CPC ................ *A61K 8/44* (2013.01); *A61K 8/345* (2013.01); *A61K 8/37* (2013.01); *A61K 8/64* (2013.01); *A61K 8/65* (2013.01); *A61K 8/97* (2013.01); *A61Q 5/002* (2013.01); *A61Q 5/004* (2013.01)

(58) Field of Classification Search
CPC . A61K 8/345; A61K 8/37; A61K 8/44; A61K 8/64; A61K 8/65; A61K 8/97; A61Q 5/002; A61Q 5/004
See application file for complete search history.

(56) References Cited

U.S. PATENT DOCUMENTS

| | | | | |
|---|---|---|---|---|
| 2009/0068255 | A1* | 3/2009 | Yu | A61K 8/0212 424/450 |
| 2009/0226537 | A1* | 9/2009 | Schmaus | A61K 8/445 424/640 |
| 2010/0215775 | A1* | 8/2010 | Schmaus | A61K 8/922 424/685 |
| 2013/0129646 | A1 | 5/2013 | Vielhaber et al. | |

FOREIGN PATENT DOCUMENTS

| | | |
|---|---|---|
| EP | 1923041 A1 | 5/2008 |
| EP | 1959915 A1 | 8/2008 |

* cited by examiner

*Primary Examiner* — Jianfeng Song
(74) *Attorney, Agent, or Firm* — Dilworth & Barrese, LLP

(57) ABSTRACT

Suggested is a blend, comprising or consisting of: (a) at least one amino acid and/or at least one protein, and (b1) at least carboxylic acid alkyl ester and/or (b2) at least one diol, and optionally (c) at least at least one additional auxiliary agent.

10 Claims, No Drawings

HAIR CARE COMPOSITION

FIELD OF INVENTION

The present invention belongs to the area cosmetics and refers to new blends for strengthening and protecting human hair.

STATE OF THE ART

A German saying concludes that often a head of golden hair is more expensive than a bag of ducats. And in fact, until 2012 the global market for hair care products is expected to reach a volume of 94 billion dollars. Particular female customers expect a constant development of modern hair care products in terms of more volume, more shine, better combability and higher protection against environmental pollution and stress. A quote from Ivana Trump takes it to the point: "Gorgeous hair is a woman's best revenge".

Taking into account the amazing growth perspective, cosmetic industry is constantly interested in new actives improving the performance of their shampoos, conditioners and all other products within the universe of hair care preparations. At the same time much R&D work is spent on already existing actives and preparation in order to find additives for synergistic improvement of their performance.

One of those well-established products are wheat bran extracts, particularly extracts of *Triticum vulgare*. These extracts are typically obtained by extraction of wheat bran by means of overcritical carbon dioxide. They provide moisture and provide softness and smooth feeling to human skin. The extracts are particular useful for making skin care products, but are also used for shampoos and treatment of scalp. However, while wheat bran extracts show interesting approaches for example with respect to hair combability, their overall performance leaves space for improvement.

Therefore, it has been the object of the present invention to develop new blends with improved performance, in particular with respect to combability, shine, luster, break extension, volume, shape retention and protection against environmental pollution and stress. One part of the object was to develop new blends based on wheat bran extracts to improve the said performances.

DESCRIPTION OF THE INVENTION

The object of the present invention is directed to a blend comprising or consisting of:
(a) at least one amino acid and/or at least one protein, and
(b1) at least one carboxylic acid alkyl ester and/or
(b2) at least one alkandiol, and optionally
(c) at least one additional auxiliary agent.

Surprisingly, it has been observed that the blends according to the present invention fulfil the complex profile and in particular simultaneously
  improve dry and wet combability
  improve shine and luster
  improve break extension
  improve volume
  improve shape retention, and
  reduce damage
of human hair, especially when formulated in hair care products. Compared to the sole ingredients the blends show a synergism (according to Kull's equation) of about 0.7, preferably this synergism is shown for proteins as compound (a), and particularly in case of wheat proteins such as wheat bran extracts.

Amino Acid

The amino acid suitable in the sense of the present invention is every amino acid which contributes to skin and hair in cosmetic point of view. Accordingly, the amino acids may be selected from the group consisting of lysine, leucine, isoleucine, phenylalanine, valine, methionine, l-arginine, threonine, histidine, tyrosine, alanine, glycine, serine, glutamic acid, aspartic acid, cysteine, proline, l-carnitine and mixtures thereof.

A preferred blend of the present invention comprises or consists of one, two, three, four, five or more of said preferred amino acids.

Amino acids are active nutrients, which are essential for hair and nails and skin, in particular in aspects of regeneration and reproduction. Thus, amino acids used in the sense of the present invention contributes to the quality of hair, nails and skin, such in that they provide shin, strong hair, strong fingernails and smooth, firm skin.

Protein

Typically, protein suitable in the sense of the present invention is every protein which contributes to skin and hair in cosmetic point of view. Accordingly, the proteins may be selected from the group consisting of wheat, elastin, collagen, milk, keratin, silk, soy, wheat germ, sodium cocoyl wheat protein. Especially preferred is wheat bran extract.

A preferred blend of the present invention comprises or consists of one, two, three, four, five or more of said preferred proteins.

Proteins are further important active nutrients in order to keep the body young and fit, to preserve skin, hair and nails remain beautiful and strong, because proteins are essential basic blocks to human body function, such as for the body tissue construction, they form important structural elements of tendons, cartilage, bone, skin, hair and nails, and are basis for the construction of antibodies.

Wheat Bran Extracts

Wheat bran means the broken coat of wheat. Wheat bran extracts are also called *Triticum vulgare* extracts (CAS 84012-44-2). They are obtainable for example by overcritical extraction of wheat bran using carbon dioxide as for example disclosed in EP 0623100 A1 (UNIVERSITY R&M).

According to the extraction conditions the extracts, which are rich in lipids, can be soluble or at least dispersible in oils or in water. A water soluble product may contain additional solvents such as for example ethylene glycol, propylene glycol or glycerol in amounts up to 25% b.w. For example, a water soluble product may contain about 30 to 35% of wheat bran extracts, about 15 to 25% b.w. propylene glycol and up to 100% b.w. water, optionally including small quantities of preservatives. An oil soluble product may contain oil bodies, such as long-chain unsaturated fatty acids or their esters. For example, an oil soluble product may contain 75 to 85% b.w. wheat bran extracts and 15 to 25% linoleic acid. Since the extracts are of plant origin, they may contain minor amounts of natural antioxidants. Preferred extracts are Biobranil® Oily and Biobranil® PGW (both SYMRISE AG).

Carboxylic Acid Esters

Typically carboxylic acid esters forming component (b1) represent alkyl esters of fatty acids. Preferably these esters follow general formula (I)

$$R^1COO-R^2 \qquad (I)$$

in which $R^1CO$ stands for a saturated or unsaturated, linear or branched acyl radical having 6 to 22 carbon atoms and $R^2$ stands for a linear or branched alkyl or alkenyl radical having 1 to 22 carbon atoms. More particularly, the blends according to the present invention comprise one or more carboxylic acid ester of formula (I) in which independently from each other $R^1CO$ stands for a saturated, linear acyl radical having 8 to 12 carbon atoms, and/or $R^2$ stands for a linear alkyl radical having 12 to 18 carbon atoms.

Suitable examples encompass esters based on the following carboxylic acids:

capronic acid, caprylic acid, nonanoic acid, caprylic acid, lauric acid, myristic acid, palmitic acid, stearic acid, oleic acid, linoleic acid, linoleic acid, arachidonic acid, gadoleic acid, behenic acid, erucic acid and their natural or technical mixtures and fractions such as coconut oil acid, palm oil acid, tallow fatty acid, olive oil acid or sunflower oil acid.

The alcohol component of said esters can be derived from methanol, ethanol, propanol, isopropyl alcohol, one of the isomeric butanols, pentanol, hexanol, heptanol, octanol, 2-ethylhexanol, nonanol, decanol, undecanol, dodecanol, tri(iso)decanol, myristyl alcohol, cetyl alcohol, stearyl alcohol, cetearyl alcohol, oleyl alcohol, linolyl alcohol, linolenyl alcohol, gadoleyl alcohol, erucyl alcohol, behenyl alcohol and their natural or technical mixtures and fractions.

Particular preferred is cetearyl nonanoate (Symmollient® S, SYMRISE AG) and 2-octyl 3,5,-triethyl hexanoat (Dragoxat® 89).

Alkandiols

The preferred alkandiols representing component (b2) are 1,2-alkandiols, preferably following general formula (II)

in which $R^3$ stands for an alkyl radical having 5 to 12 carbon atoms. Particular preferred are the following species: 1,2-pentandiol (Hydrolite® 5, SYMRISE AG), 1,2-hexandiol, 1,2-octan-diol or a binary (Symdiol® 68, SYMRISE AG) or ternary mixture of these compounds. Said alkandiols, particular mixtures of two or three of them, are well-known cosmetic ingredients, which are often used for improving antimicrobial protection of a cosmetic composition (EP 1478231 B1, SYMRISE). Preferred is 1,2-pentandiol (Hydrolite® 5, SYMRISE AG) and/or a mixture of 1,2-hexandiol and 1,2-octandiol (Symdiol® 68).

Auxiliary Agent

The blend of the present invention may comprise or consist of compounds (a), (b1) and (b2), but it is also possible that they encompass additional auxiliary agents as compound (c). A preferred blend of the present invention comprises or consists of one, two, three, four, five or more of additional auxiliary agents. Preferably, the additional auxiliary agents (compound (c)) are selected from water, aliphatic alcohols as for example ethanol, or polyols such as ethylene glycol, propylene glycol or glycerol, oil bodies, and other lipophilic additives like antioxidants, extracts and the like.

In case compound (a) is water soluble or at least water dispersible the mixture may comprise solvents as additional auxiliary agents (compound (c)) such as water, aliphatic alcohols as for example ethanol, or polyols such as ethylene glycol, propylene glycol or glycerol.

In case the mixtures, respectively compound (a) is soluble or dispersible in lipids, they may comprise as additional auxiliary agents (compound (c)) oil bodies, and other lipophilic additives like antioxidants, extracts and the like.

Mixtures

The amounts of the compounds (a) to (c) in a blend of the present invention are preferably (i) from 5% b.w. to 50% b.w., preferably from 10% b.w. to from 45% b.w., more preferably from 10% b.w. to 40% b.w. of compound(s) (a), (ii) from 10% b.w. to 70% b.w., preferably from 15% b.w. to 65% b.w., more preferably from 20% b.w. to 60% b.w. of compound(s) (b1), (iii) from 0.1% b.w. to 70% b.w., preferably from 1% b.w. to 60% b.w., more preferably from 1% b.w. to 50% b.w. of a compound(s) (b2), (iv) from 0.001% b.w. to 20% b.w., preferably from 0.01% b.w. to 15% b.w., more preferably from 0.1% b.w. to 10% b.w. of compound(s) (c), on condition that all compounds (a to c each if present in the mixture) add together to 100% b.w. based on the total amount of the blend.

Especially preferred is a blend which comprises or consists of (i) from 5% b.w. to 50% b.w., preferably from 10% b.w. to from 45% b.w., more preferably from 10% b.w. to 40% b.w. of compound(s) (a), (ii) from 10% b.w. to 70% b.w., preferably from 15% b.w. to 65% b.w., more preferably from 20% b.w. to 60% b.w. of compound(s) (b1), (iii) from 0.001% b.w. to 20% b.w., preferably from 0.01% b.w. to 15% b.w., more preferably from 0.1% b.w. to 10% b.w. of compound(s) (c), on condition that all compounds (a to c each if present in the mixture) add together to 100% b.w. based on the total amount of the blend.

Also especially preferred is a blend which comprises or consists of (i) from 5% b.w. to 50% b.w., preferably from 10% b.w. to from 45% b.w., more preferably from 10% b.w. to 40% b.w. of compound(s) (a), (ii) from 10% b.w. to 70% b.w., preferably from 15% b.w. to 65% b.w., more preferably from 20% b.w. to 60% b.w. of compound(s) (b1), (iii) from 0.1% b.w. to 70% b.w., preferably from 1% b.w. to 60% b.w., more preferably from 1% b.w. to 50% b.w. of a compound(s) (b2), on condition that all compounds (a to b each if present in the mixture) add together to 100% b.w. based on the total amount of the blend.

Also especially preferred is a blend which comprises or consists of (i) from 5% b.w. to 50% b.w., preferably from 10% b.w. to from 45% b.w., more preferably from 10% b.w. to 40% b.w. of compound(s) (a), (ii) from 0.1% b.w. to 70% b.w., preferably from 1% b.w. to 60% b.w., more preferably from 1% b.w. to 50% b.w. of a compound(s) (b2), (iii) from 0.001% b.w. to 20% b.w., preferably from 0.01% b.w. to 15% b.w., more preferably from 0.1% b.w. to 10% b.w. of compound(s) (c), on condition that all compounds (a to c each if present in the mixture) add together to 100% b.w. based on the total amount of the blend.

The preferred mixtures of the present invention show to be particular advantageously in fulfilling the profile as mentioned beforehand to human hair and hair products.

In a preferred embodiment the blend of the present invention may comprise said components (a) and (b1+b2) in a ratio by weight from about 1:5 to about 5:1, preferably from about 1:3 to about 3:1, more preferably from about 1:2 to about 2:1. Most preferred is a ratio by weight that is about 1:1.

In case the blend encompasses compounds (b1) and (b2) their ratio by weight may reach from about 1:10 to about 10:1, preferably from about 1:5 to about 5:1 and more preferably from about 1:2 to about 2:1.

In a preferred embodiment a blend of the present invention comprises or consists of compounds (a+b1+b2) which are present in the blend at least to about 50% b.w., preferably at least 60% b.w., and more preferably of at least 70% b.w. of the blend.

In case the amount of compounds (a+b1+b2) is 50%, the amount of compound (c) is 50% in the blends. In case (a+b1+b2) is 60%, the amount of compound (c) is 40% in the blends. In case (a+b1+b2) is 70%, the amount of compound (c) is 30% in the blends.

Particularly, in a preferred embodiment a typical blend of the present invention contains or consists of about 70 to 80% of compounds (a+b1+b2) and of about 20% b.w. to 30% b.w. additional auxiliary agent (compound (c)), respectively 70% b.w. to 80% b.w. of compounds (a+b1) and of about 20% b.w. to 30% b.w. additional auxiliary agent (compound (c)), respectively 70% b.w. to 80% b.w. of compounds (a+b2) and of about 20% b.w. to 30% b.w. additional auxiliary agent (compound (c)), In further embodiments the blends of the present invention comprise or consist of compounds (a) and (b2) and (c) or compounds (a) and (b1) and (c). The amounts for the compounds are as described above and also apply here.

Particularly preferred is a blend of the present which comprises or consists of compounds (a) and (b1) and (c), wherein compound (a) is preferably a wheat bran extract, compound (b1) is preferably cetearyl nonanoate (Symmollient® S) and/or 2-octyl 3,5,5-trimethyl hexanoate (Dragoxat® 89), and compound (c) is preferably selected from the group consisting of oil bodies, lipophilic additives like antioxidants and extracts. Most preferred are oil bodies and antioxidants with fat-soluble properties as compound (c), and especially preferred alpha-tocopherol and/or camilia olifeira seed oil.

Particularly preferred blend comprise or consist of a compound (a) that is preferably a wheat bran extract, compound (b2) that is preferably 1,2 pentandiol and/or 1,2-hexandiol and/or 1,2-octandiol (Symdiol® 68) and compound (c) that is preferably selected from the group consisting of water, aliphatic alcohols as for example ethanol, or polyols such as ethylene glycol, propylene glycol or glycerol. Most preferred are water and/or glycerol.

Hair Care and Personal Care Compositions

Another object of the present invention refers to a hair care or personal care composition, comprising a blend of the present invention as defined above in a working amount, for example about 0.1 to about 10% b.w., preferably about 0.5 to about 8% b.w. and particularly from about 1 to about 5% b.w., and most preferably from about 2 to 3% b.w.— calculated on the hair care or personal care composition(s). The hair care or personal care composition may represent for example a cosmetic cream, lotion, spray, emulsion, ointment, gel or mouse and the like. Typical examples are hair shampoos, hair conditioners and corresponding "2-in-1" products.

The hair care or personal care preparations according to the invention may contain antidandruff agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, hair promotion agents, cooling agents, skin-cooling agents, warming agents, skin-warming agents, stabilizers, UV-absorbing agents, UV filters, detergents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, odoriferous substances, polyols, surfactants, electrolytes, organic solvents or silicone derivatives and the like as additional auxiliaries and additives.

A preferred embodiment is directed to a hair care or personal care composition, comprising said blends of the present invention (comprising or consisting of compounds (a) to (c)) and further ingredients, which are typical for hair care or personal care compositions as described above and further defined in detail below.

Surfactans

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:
  products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
  $C_{12/18}$ fatty acid monoesters and diesters of addition products of 1 to 30 mol ethylene oxide onto glycerol;
  glycerol mono- and diesters and sorbitan mono- and diesters of saturated and unsaturated fatty acids containing 6 to 22 carbon atoms and ethylene oxide addition products thereof;
  addition products of 15 to 60 mol ethylene oxide onto castor oil and/or hydrogenated castor oil;
  polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
  addition products of 2 to 15 mol ethylene oxide onto castor oil and/or hydrogenated castor oil;
  partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);
  mono-, di and trialkyl phosphates and mono-, di- and/or tri-PEG-alkyl phosphates and salts thereof;
  wool wax alcohols;
  polysiloxane/polyalkyl polyether copolymers and corresponding derivatives;
  mixed esters of pentaerythritol, fatty acids, citric acid and fatty alcohol and/or mixed esters of $C_{6-22}$ fatty acids, methyl glucose and polyols, preferably glycerol or polyglycerol,
  polyalkylene glycols and
  glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan®

PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers.

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric Emulsifiers.

Other suitable emulsifiers are amphboteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkyl-aminopropionic acids and alkylaminoacetic acids containing around 8 to 18 carbon atoms in the alkyl group. Particularly preferred ampholytic surfactants are N-cocoalkylamino-propionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohy-droxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C.-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacryl-amide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan® HMS)
salicylic acid-2-ethylhexyl ester (Neo Heliopan® OS)
triethanolamine salicylate
4-isopropyl benzyl salicylate
anthranilic acid menthyl ester (Neo Heliopan® MA)
diisopropyl cinnamic acid ethyl ester
p-methoxycinnamic acid-2-ethylhexyl ester (Neo Heliopan® AV)
diisopropyl cinnamic acid methyl ester
p-methoxycinnamic acid isoamyl ester (Neo Heliopan® E 1000)
p-methoxycinnamic acid diethanolamine salt
p-methoxycinnamic acid isopropyl ester
2-phenylbenzimidazole sulfonic acid and salts (Neo Heliopan® Hydro)
3-(4'-trimethylammonium) benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan® MBC)
3-benzylidene-D,L-camphor
N-[(2 and 4)-[2-(oxoborn-3-ylidene) methyl]benzyl] acrylamide polymer
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb® HEB)
benzylidene malonate polysiloxane (Parsol® SLX)
glyceryl ethylhexanoate dimethoxycinnamate
dipropylene glycol salicylate
tris(2-ethylhexyl)-4,4',4"-(1,3,5-triazine-2,4,6-triyltriimino) tribenzoate (=2,4,6-trianilino-(p-carbo-2'-ethylhexyl-1'-oxy)-1,3,5-triazine) (Uvinul® T150).

Broadband filters which are preferably combined with one or more compounds of formula (I) in a preparation according to the present invention are selected from the group consisting of
2-ethylhexyl-2-cyano-3,3-diphenyl acrylate (Neo Heliopan® 303)
ethyl-2-cyano-3,3'-diphenyl acrylate
2-hydroxy-4-methoxybenzophenone (Neo Heliopan® BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-di methoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3 (1,3,3,3-tetramethyl-1-(trime-thylsilyl)oxy)disiloxanyl) propyl) (Mexoryl® XL)
2,2'-methylene bis-(6-(2H-benzotriazol-2-yl)-4-1,1,3,3-tetramethylbutyl) phenol) (Tinosorb® M)
2,4-bis-[4-(2-ethylhexyloxy)-2-hydroxyphenyl]-1,3,5-triazine 2,4-bis-[{(4-(2-ethylhexyloxy)-2-hydroxy}phenyl]-6-(4-methoxyphenyl)-1,3,5-triazine
(Tinosorb® S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl) phenylamino]-1,3,5-triazine
2,4-bis-[{4-(3-(2-propyloxy)-2-hydroxypropyloxy)-2-hydroxy}phenyl]-6-[4-(2-ethylcarboxyl) phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2"-methyl-propyloxy)-2-hydroxy}phenyl]-6-(4-methoxyphenyl)-1,3,5-triazine.

The compositions can comprise further typical detergent and cleansing composition ingredients such as UV-A filters filters which are preferably combined with one or more compounds of formula (I) in a preparation according to the present invention are selected from the group consisting of
4-isopropyl dibenzoyl methane
terephthalylidene dibornane sulfonic acid and salts (Mexoryl® SX)
4-t-butyl-4'-methoxydibenzoyl methane (avobenzone)/(Neo Heliopan® 357)
phenylene bis-benzimidazyl tetrasulfonic acid disodium salt (Neo Heliopan® AP)
2,2'-(1,4-phenylene)-bis-(1H-benzimidazole-4,6-disulfonic acid), monosodium salt
2-(4-diethylamino-2-hydroxybenzoyl) benzoic acid hexyl ester (Uvinul A Plus)
indanylidene compounds in accordance with DE 100 55 940 A1 (=WO 2002 038537 A1)

The compositions can comprise further typical detergent and cleansing composition ingredients such as UV filters which are more preferably combined with one or more compounds of formula (I) in a preparation according to the present invention are selected from the group consisting of
p-aminobenzoic acid
3-(4'-trimethylammonium) benzylidene bornan-2-one methyl sulfate
salicylic acid homomenthyl ester (Neo Heliopan® HMS)
2-hydroxy-4-methoxybenzophenone (Neo Heliopan® BB)
2-phenylbenzimidazole sulfonic acid (Neo Heliopan® Hydro)
terephthalylidene dibornane sulfonic acid and salts (Mexoryl® SX)
4-tert-butyl-4'-methoxydibenzoyl methane (Neo Heliopan® 357)
3-(4'-sulfo)benzylidene bornan-2-one and salts
2-ethylhexyl-2-cyano-3,3-diphenyl acrylate (Neo Heliopan® 303)
N-[(2 and 4)-[2-(oxoborn-3-ylidene) methyl]benzyl] acrylamide polymer
p-methoxycinnamic acid-2-ethylhexyl ester (Neo Heliopan® AV)
p-aminobenzoic acid ethyl ester (25 mol) ethoxylated (INCI name: PEG-25 PABA)
p-methoxycinnamic acid isoamyl ester (Neo Heliopan® E1000)
2,4,6-trianilino-(p-carbo-2'-ethylhexyl-1'-oxy)-1,3,5-triazine (Uvinul® T150)
phenol, 2-(2H-benzotriazol-2-yl)-4-methyl-6-(2-methyl-3 (1,3,3,3-tetramethyl-1-(trime-thylsilyl)oxy)disiloxyanyl) propyl) (Mexoryl® XL)
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan® MBC)
3-benzylidene camphor
salicylic acid-2-ethylhexyl ester (Neo Heliopan® OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetra methyl butyl) phenol) (Tinosorb® M)
phenylene bis-benzimidazyl tetrasulfonic acid disodium salt (Neo Heliopan® AP)
2,4-bis-[{(4-(2-ethylhexyloxy)-2-hydroxy}phenyl]-6-(4-methoxyphenyl)-1,3,5-triazine (Tinosorb® S)
benzylidene malonate polysiloxane (Parsol® SLX)
menthyl anthranilate (Neo Heliopan® MA)
2-(4-diethylamino-2-hydroxybenzoyl) benzoic acid hexyl ester (Uvinul® A Plus)
indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Hair Pigmentation

Preferred active ingredients for hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, *papaya* extract, turmeric extract, mulberry extract, bengkoang extract, nutgrass extract, liquorice root extract or constituents concentrated or isolated therefrom, preferably glabridin or licochalcone A, *artocarpus* extract, extract of *rumex* and *ramulus* species, extracts of pine species (*pinus*), extracts of *vitis* species or stilbene derivatives isolated or concentrated therefrom, saxifrage extract, scutelleria extract, grape extract and/or microalgae extract, in particular *Tetraselmis suecica* Extract.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the *chrysanthemum* species, san-guisorba species, walnut extracts, urucum extracts, rhubarb extracts, microalgae extracts, in particular *Isochrysis galbana*, trehalose, erythru-lose and dihydroxyacetone. Flavonoids which bring about skin and hair tinting or brown-ing (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro- 1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (Leontodon or *Taraxacum*), Orthosiphon, Vitex, *Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis, Isochrysis galbana*, licorice, grape, apple, barley or hops or/nd hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnema sylvestre*.

Physiological Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (l-menthoxy)-1,2-propandiol, (1-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy) acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N$^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (l-(–)-isopulegol, 1-(–)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

Anti-Inflammatory Agents

Suitable anti-inflammatory agents may be selected from the group formed by:
(i) steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone,
(ii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone,
(iii) natural or naturally occuring anti-inflammatory substances or substances that alleviate reddening and/or itching, in particular extracts or fractions from camomile, Aloe vera, *Commiphora* species, *Rubia* species, willow, willow-herb, oats, calendula, *arnica*, St John's wort, honeysuckle, rosemary, *Passiflora incarnata*, witch hazel, ginger or *Echinacea*, or single active compounds thereof,
(iv) histamine receptor antagonists, serine protease inhibitors (e.g. of Soy extracts), TRPV1 antagonists (e.g. 4-t-Butylcyclohexanol), NK1 antagonists (e.g. Aprepitant, Hydroxyphenyl Propamidobenzoic Acid), cannabinoid receptor agonists (e.g. Palmitoyl Ethanolamine) and TRPV3 antagonists.

Physiological Cooling Agents

Suitable physiological cooling agents may be selected from the group consisting of menthol, menthone glycerol acetal, menthone glyceryl ketal, menthyl lactate preferably l-menthyl lactate, in particular l-menthyl 1-lactate), menthyl ethyl oxamate, substituted menthyl-3-carboxylic acid amides (e.g. menthyl-3-carboxylic acid N-ethylamide, N$^\alpha$-(L-menthanecarbonyl)glycine ethyl ester, 2-isopropyl-N-2,3-trimethylbutanamide, substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, isopulegol, menthyl hydroxycarboxylic acid esters (e.g. menthyl 3-hydroxybutyrate), monomenthyl succinate, monomenthyl glutarate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl 3,6-di- and -trioxaalkanoates, 3-menthyl methoxyacetate and icilin.

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or *styrax* or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, *galbanum* oil, labdanum oil and lavandin oil. Preference is given to using bergamot oil, dihydromyrcenol, lilial, lyral, citronellol, phenylethyl alcohol, a-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, *angelica*, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (*galbanum*, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, •-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, *galbanum* oil, *ladanum* oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

INDUSTRIAL APPLICATION

A further important aspect of the invention are cosmetic preparations, especially hair care or personal care preparations, such as cosmetic cream, lotion, spray, emulsion, ointment, gel or mouse, particularly preferred are hair shampoos, hair conditioners and corresponding "2-in-1" products comprising the blend in accordance to the present invention and as described above.

In particular preferred are hair care preparations comprising
(a) from 0.1 to about 10% b.w., preferably about 0.5 to about 8% b.w. and particularly from about 1 to about 5% b.w., and most preferably from about 2 to 3% of a blend in accordance to the present invention and as described above,
(b) from about 1% b.w. to about 50% b.w. of a solubilizing agent, wherein the solubilizing agent is a hydrophilic solvent and/or lipophilic solvent,
(c) from about 0.5% b.w. to about 20% b.w. of a rheology modifier,
(d) at least 20% b.w., more preferably at least 30% b.w. of an aqueous carrier, and
(e) optionally from about 0.01% b.w. to about 40% b.w. further additives.

Especially suitable hydrophilic solvents in the sense of the present invention are selected from the group consisting of alcohols, diols, polyols, phenols or esters with good solubilizing properties, preferably selected from the group consisting of ethanol, 1-propanol, isopropanol phenoxyethanol, benzyl alcohol, ethylene glycol, propylene glycol, 1,3-propanediol, butylene glycol, pentylene glycol, 1,2-hexanediol, hexylene glycol dipropylene glycol, ethoxydiglycol, propylene carbonate, glycerine carbonate, butylene carbonate, triethyl citrate, ethyl lactate, butyl lactate, ethylacetate, diethylmalonate, diacetin, dimethyl isosorbide, diethylene glycol, PPG-3 methyl ether or any of their mixtures.

Especially suitable lipophilic solvents in the sense of the present invention are selected from the group consisting of 2-methyl-5-cyclohexylpentanol, 2-methyl 5-phenylpentanol, dimethyl phenylpropanol, dimethyl phenylbutanol, 3-methyl-4-phenylbutan-2-ol, phenylisohexanol, iso adipate, farnesol, 4-hydroxyacetophenone, cetearyl ethylhexanoate, triisononanoin, caprylic/capric triglycerides, glyceryl caprylate, glyceryl caprate, glyceryl laurate, decyl alcohol, lauryl alcohol, cetyl alcohol, hexyldecanol, ethylhexyl isononanoate, ethylhexylglycerin, diethyl succinate, caprylyl glycol, decylene glycol, phenylpropanol, menthyl antranilate, homosalate, ethylhexyl salicylate, benzyl benzoate, benzyl salicylate, diethylhexyl 2,6-naphthalate, 2-benzylheptanol, isopropyl myristate, isopropyl palmitate, methyldihydrojasmonate, tetramethyl acetyloctahydronaphthalenes, trimethylben-zenepropanol, ethylbutyrate, menthyl acetate, carvacrol, methylsalicylate, eugenol, menthone, carvone, anethole, cinnamic aldehyde, limonene, isoamylacetate, dihydromyrcenol, methyldihydrojasmonate (Hedione), tetramethyl acetyloctahydro-naphtalenes (Iso E super), isosorbide dicyprylate, menthone glycerin acetal, mentyl lactate, phenyl salicylate, farnesyl acetate, ethyl laurate, phenethyl benzoate, *Persea gratissima* (avocado oil), isoamyl-p methoxycinnamate, 4-methylbenzylidene camphor, ethylhexyl methoxycinnamate or any of their mixtures. Further suitable lipophilic solvents are oil bodies as described above.

The rheology modifier is preferably a thickening agent or rheology additive as described above.

The further additives are described above and may be selected from antidandruff agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, moisturizing creams, ointments, opacifying agents, plasticizing agents, covering agents, polish, gloss agents, polymers, powders, proteins, re-oiling agents, abrading agents, silicones, hair promotion agents, cooling agents, skin-cooling agents, warming agents, skin-warming agents, stabilizers, UV-absorbing agents, UV filters, detergents, vitamins, oils, waxes, fats, phospholipids, saturated fatty acids, mono- or polyunsaturated fatty acids, a-hydroxy acids, polyhydroxyfatty acids, dyestuffs, colour-protecting agents, pigments, odoriferous substances.

Another object of the present invention refers to a method for strengthening and protecting human hair, comprising the following steps:
(i) providing a blend in accordance to the present invention and as defined above, and
(ii) incorporating said blend into a hair care or personal care composition, and (iii) bringing said hair care or personal care composition into contact with human hair.

Finally, the invention also encompasses the use of said blends for improving and strengthening human hair.

The preferred embodiments, particularly combinations of compounds and their ratios as explained in the earlier sections, shall also refer to the method and the use claimed above. Therefore, repeating these statements is not necessary.

In the following, the invention is illustrated in more detail by various working examples, without limiting the invention to these specific embodiments.

EXAMPLES

Examples 1 to 16, Comparative Examples C1 to C4

Hair Combability

Hair combability test measures the force required for standard comb to pass through a hair tress. The parameter measured is:

- Total work: the total energy required during the whole combing process (Joules)
- Peak of Force: the maximum force registered during the combing process (gmf)

Since the hair surface characteristics are dependent on the cuticle/comb interaction, hair in wet or dry situations can change the values in the measurements. Caucasian bleached tresses were treated 5 times with the samples. Test in wet condition was performed. The tresses were dried at controlled temperature and humidity (22° C.+/−2° C. and 55% RH) overnight before evaluation in dry condition. Comparisons among the samples were made. Statistical analysis was performed with analysis of variance, followed by post-test of Tukey, considering 95% of confidence interval. The blends were incorporated at specific concentrations in shampoo and conditioner formulations: example 1=0.1% b.w. in shampoo and 0.5% b.w. in conditioner; example 2=1.0% b.w. in shampoo and 1.0% b.w. in conditioner. Pure ingredients were incorporated at half of its respective blend, i.e.: SymMollient S=0.05% b.w. in shampoo and 0.25% b.w. in conditioner; Biobranil Oily=0.05% b.w. in shampoo and 0.25% b.w. in conditioner; Hydrolite 5=0.5% b.w. in shampoo and 0.5% b.w. in conditioner; and finally Biobranil PGW=0.5% b.w. in shampoo and 0.5% b.w. in conditioner. The results are compiled in Table 1a to 1c. Examples 1 to 16 are according to the invention, examples C1 to C4 serve for comparison. The values express the percentage of improvement when compared to placebo.

TABLE 1a

Results hair combability test (amounts in % b.w.)

| Compounds | C1 | C2 | C3 | C4 | 1 | 2 |
|---|---|---|---|---|---|---|
| Wheat bran extracts Biobranil ® Oily | 100.00 | — | — | — | 39.45 | — |
| Wheat bran extracts Biobranil ® PGW | — | 100.00 | — | — | — | 10.00 |
| Cetearyl Nonanoate Symmollient ® S | — | — | 100.00 | — | 39.45 | — |
| 1,2-Pentandiol Hydrolite ® 5 | — | — | — | 100.00 | — | 50.00 |
| 1,2-Hexanediol/1,2-Octanediol Symdiol ® 68 | — | — | — | — | — | 1.00 |
| 2-Octyl 3,5,5-trimethyl hexanoate Dragoxat ® 89 | — | — | — | — | 20.00 | — |
| Camillia Olifeira Seed Oil | — | — | — | — | 1.00 | — |
| Alpha-Tocopherol | — | — | — | — | 0.10 | — |
| Glycerol | — | — | — | — | — | 10.00 |
| Water | — | — | — | — | — | 29.00 |
| Dry combability | | | | | | |
| Shampoo formulation | +17 | +14 | +4 | +16 | +33 | +30 |
| Shampoo/Conditioner composition | | | | | +32 | +35 |
| Wet combability | | | | | | |
| Shampoo formulation | +8 | +5 | 0 | +2 | +35 | +30 |
| Shampoo/Conditioner composition | | | | | +16 | +15 |

TABLE 1b

Results hair combability test (amounts in % b.w.)

| Compounds | 3 | 4 | 5 | 6 | 7 | 8 | 9 |
|---|---|---|---|---|---|---|---|
| Wheat bran extracts Biobranil ® Oily | 39.45 | — | — | — | 39.45 | — | — |
| Wheat bran extracts Biobranil ® PGW | — | 10.00 | — | — | — | 10.00 | |
| Keratin | — | — | 39.45 | 35.00 | — | — | 20.00 |
| Silk | — | — | — | 10.00 | — | — | 10.00 |
| 1-Arginine | — | — | — | — | 1.00 | 1.00 | 1.00 |
| Glutamic acid | — | — | — | 1.00 | — | 1.00 | 1.00 |
| Tyrosine | — | — | — | — | — | — | — |
| Cysteine | — | — | — | — | — | — | — |

TABLE 1b-continued

Results hair combability test (amounts in % b.w.)

| Compounds | 3 | 4 | 5 | 6 | 7 | 8 | 9 |
|---|---|---|---|---|---|---|---|
| Cetearyl Nonanoate Symmollient ® S | 39.45 | — | — | 35.50 | 39.45 | — | 15.00 |
| 1,2-Pentandiol Hydrolite ® 5 | — | 40.00 | 15.55 | — | — | 50.00 | 5.00 |
| 1,2-Hexanediol/1,2-Octanediol Symdiol ® 68 | 20.00 | — | 5.00 | — | 19.00 | 1.00 | 10.00 |
| 2-Octyl 3,5,5-trimethyl hexanoate Dragoxat ® 89 | — | 10.00 | — | 17.00 | — | — | — |
| Camillia Olifeira Seed Oil | 1.00 | — | — | 1.00 | 1.00 | — | 0.50 |
| Alpha-Tocopherol | 0.10 | — | — | 0.50 | 0.10 | — | 0.50 |
| Glycerol | — | 10.00 | 10.00 | — | — | 10.00 | 10.00 |
| Water | — | 30.00 | 30.00 | — | — | 27.00 | 27.00 |
| Dry combability | | | | | | | |
| Shampoo formulation | +33 | +30 | +33 | +35 | +33 | +32 | +35 |
| Shampoo/Conditioner composition | +30 | +32 | +35 | +32 | +30 | +35 | |
| Wet combability | | | | | | | |
| Shampoo formulation | +30 | +30 | +33 | +35 | +35 | +35 | +35 |
| Shampoo/Conditioner composition | +15 | +17 | +15 | +20 | +20 | +16 | |

TABLE 1c

Results hair combability test (amounts in % b.w.)

| Compounds | 10 | 11 | 12 | 13 | 14 | 15 | 16 |
|---|---|---|---|---|---|---|---|
| Wheat bran extracts Biobranil ® Oily | 29.45 | — | 29.00 | 29.00 | — | — | — |
| Wheat bran extracts Biobranil ® PGW | — | 29.45 | — | — | 29.00 | — | — |
| Keratin | 10.00 | — | 10.00 | 5.00 | 5.00 | 25.00 | — |
| Silk | — | 10.00 | — | 5.00 | 5.00 | — | — |
| 1-Arginine | — | — | 1.00 | — | — | 0.50 | 2.50 |
| Glutamic acid | — | — | — | — | 0.50 | 0.50 | 2.50 |
| Tyrosine | — | — | — | 0.50 | — | 0.50 | 2.50 |
| Cysteine | — | — | — | 0.50 | 0.50 | 0.50 | 2.50 |
| Cetearyl Nonanoate Symmollient ® S | 25.45 | 25.45 | 10.00 | 10.00 | 10.00 | 13.00 | 20.00 |
| 1,2-Pentandiol Hydrolite ® 5 | — | — | 10.00 | 10.00 | 10.00 | 10.00 | 20.00 |
| 1,2-Hexanediol/1,2-Octanediol Symdiol ® 68 | 2.00 | 2.00 | 5.00 | 5.00 | 5.00 | 5.00 | 10.00 |
| 2-Octyl 3,5,5-trimethyl hexanoate Dragoxat ® 89 | — | — | 5.00 | 5.00 | 5.00 | 5.00 | — |
| Camillia Olifeira Seed Oil | 1.00 | 1.00 | 0.50 | 0.50 | 0.50 | 0.50 | 0.50 |
| Alpha-Tocopherol | 0.10 | 0.10 | 0.50 | 0.50 | 0.50 | 0.50 | 0.50 |
| Glycerol | 10.00 | 10.00 | 5.00 | 5.00 | 5.00 | 5.00 | 10.00 |
| Water | 22.00 | 22.00 | 24.00 | 24.00 | 24.00 | 34.00 | 29.00 |
| Dry combability | | | | | | | |
| Shampoo formulation | +33 | +33 | +34 | +37 | +37 | +32 | +30 |
| Shampoo/Conditioner composition | | | +30 | +35 | +32 | +35 | |
| Wet combability | | | | | | | |
| Shampoo formulation | +30 | +30 | +33 | +35 | +35 | +30 | +25 |
| Shampoo/Conditioner composition | | | | +25 | +25 | +15 | |

The examples and comparison examples clearly indicate that adding certain diols and/or esters improve dry and wet combability in different consumer formulations in synergistic manner.

Examples 17 to 32, Comparative Examples C5 to C8

Luster Evaluation

Luster evaluation test analyzes luster effect by the interactions of the light with the hair surface. The measurement is made using SAMBA system and the results are expressed by:

Shine: intensity of the reflection of the light at the hair surface—first reflection of the light.

Luster: parameter calculated from values of shine, chroma and diffused light to express the luster effect seen by an observer.

Caucasian bleached tresses were treated 5 times with the samples. The tresses were dried at controlled temperature and humidity (22° C.+/−2° C. and 55% RH) overnight before evaluation. Comparisons among the samples were made. Statistical analysis was performed with analysis of variance, followed by post-test of Tukey, considering 95% of confidence interval. The blends were incorporated at specific concentrations in shampoo and conditioner formulations: example 1=0.1% b.w. in shampoo and 0.5% b.w. in conditioner; example 2=1.0% b.w. in shampoo and 1.0% b.w. in conditioner. Pure ingredients were incorporated at half of its respective blend, i.e.: SymMollient S=0.05% b.w. in shampoo and 0.25% b.w. in conditioner; Biobranil Oily=0.05% b.w. in shampoo and 0.25% b.w. in conditioner; Hydrolite 5=0.5% b.w. in shampoo and 0.5% b.w. in conditioner; and finally Biobranil PGW=0.5% b.w. in shampoo and 0.5% b.w. in conditioner The results are compiled in Table 2a to 2c. Examples 17 to 32 are according to the invention, examples C5 to C8 serve for comparison. The values express the percentage of improvement when compared to placebo.

TABLE 2a

Results luster evaluation (amounts in % b.w.)

| Compounds | C5 | C6 | C7 | C8 | 17 | 18 |
|---|---|---|---|---|---|---|
| Wheat bran extracts Biobranil ® Oily | 100.00 | — | — | — | 39.45 | — |
| Wheat bran extracts Biobranil ® PGW | — | 100.00 | — | — | — | 10.00 |
| Cetearyl Nonanoate Symmollient ® S | — | — | 100.00 | — | 39.45 | — |
| 1,2-Pentandiol Hydrolite ® 5 | — | — | — | 100.00 | — | 50.00 |
| 1,2-Hexanediol/1,2-Octanediol Symdiol ® 68 | — | — | — | — | — | 1.00 |
| 2-Octyl 3,5,5-trimethyl hexanoate Dragoxat ® 89 | — | — | — | — | 20.00 | — |
| Camillia Olifeira Seed Oil | — | — | — | — | 1.00 | — |
| Alpha-Tocopherol | — | — | — | — | 0.10 | — |
| Glycerol | — | — | — | — | — | 10.00 |
| Water | — | — | — | — | — | 29.00 |
| Shine | | | | | | |
| Shampoo formulation | +7 | +5 | 0 | 0 | +49 | +14 |
| Luster | | | | | | |
| Shampoo formulation | | | | | +16 | |
| Shampoo/Conditioner composition | | | | | +24 | |

TABLE 2b

Results luster evaluation (amounts in % b.w.)

| Compounds | 19 | 20 | 21 | 22 | 23 | 24 | 25 |
|---|---|---|---|---|---|---|---|
| Wheat bran extracts Biobranil ® Oily | 39.45 | — | — | — | 39.45 | — | — |
| Wheat bran extracts Biobranil ® PGW | — | 10.00 | — | — | — | 10.00 | — |
| Protein 1 | — | — | 39.45 | 35.00 | — | — | 20.00 |
| Protein 2 | — | — | — | 10.00 | — | — | 10.00 |
| Amino acid 1 | — | — | — | — | 1.00 | 1.00 | 1.00 |
| Amino acid 2 | — | — | — | 1.00 | — | 1.00 | 1.00 |
| Cetearyl Nonanoate Symmollient ® S | 39.45 | — | — | 35.50 | 39.45 | — | 15.00 |
| 1,2-Pentandiol Hydrolite ® 5 | — | 40.00 | 15.55 | — | — | 50.00 | 5.00 |
| 1,2-Hexanediol/1,2-Octanediol Symdiol ® 68 | 20.00 | — | 5.00 | — | 19.00 | 1.00 | 10.00 |
| 2-Octyl 3,5,5-trimethyl hexanoate Dragoxat ® 89 | — | 10.00 | — | 17.00 | — | — | — |

TABLE 2b-continued

Results luster evaluation (amounts in % b.w.)

| Compounds | 19 | 20 | 21 | 22 | 23 | 24 | 25 |
|---|---|---|---|---|---|---|---|
| Camillia Olifeira Seed Oil | 1.00 | — | — | 1.00 | 1.00 | — | 0.50 |
| Alpha-Tocopherol | 0.10 | — | — | 0.50 | 0.10 | — | 0.50 |
| Glycerol | — | 10.00 | 10.00 | | — | 10.00 | 10.00 |
| Water | — | 30.00 | 30.00 | | — | 27.00 | 27.00 |
| Shine | | | | | | | |
| Shampoo formulation | +20 | +25 | +20 | +45 | +40 | +30 | +35 |
| Shampoo formulation | | | +20 | +10 | +15 | | |
| Luster | | | | | | | |
| Shampoo/Conditioner composition | | | +16 | −16 | +10 | | |

TABLE 2c

Results luster evaluation (amounts in % b.w.)

| Compounds | 26 | 27 | 28 | 29 | 30 | 31 | 32 |
|---|---|---|---|---|---|---|---|
| Wheat bran extracts Biobranil ® Oily | 29.45 | — | 29.00 | 29.00 | — | — | — |
| Wheat bran extracts Biobranil ® PGW | — | 29.45 | — | — | 29.00 | — | — |
| Keratin | 10.00 | — | 10.00 | 5.00 | 5.00 | 25.00 | — |
| Silk | — | 10.00 | — | 5.00 | 5.00 | — | — |
| l-Arginine | — | — | 1.00 | — | — | 0.50 | 2.50 |
| Glutamic acid | — | — | — | — | 0.50 | 0.50 | 2.50 |
| Tyrosine | — | — | — | 0.50 | — | 0.50 | 2.50 |
| Cysteine | — | — | — | 0.50 | 0.50 | 0.50 | 2.50 |
| Cetearyl Nonanoate Symmollient ® S | 25.45 | 25.45 | 10.00 | 10.00 | 10.00 | 13.00 | 20.00 |
| 1,2-Pentandiol Hydrolite ® 5 | — | — | 10.00 | 10.00 | 10.00 | 10.00 | 20.00 |
| 1,2-Hexanediol/1,2-Octanediol Symdiol ® 68 | 2.00 | 2.00 | 5.00 | 5.00 | 5.00 | 5.00 | 10.00 |
| 2-Octyl 3,5,5-trimethyl hexanoate Dragoxat ® 89 | — | — | 5.00 | 5.00 | 5.00 | 5.00 | — |
| Camillia Olifeira Seed Oil | 1.00 | 1.00 | 0.50 | 0.50 | 0.50 | 0.50 | 0.50 |
| Alpha-Tocopherol | 0.10 | 0.10 | 0.50 | 0.50 | 0.50 | 0.50 | 0.50 |
| Glycerol | 10.00 | 10.00 | 5.00 | 5.00 | 5.00 | 5.00 | 10.00 |
| Water | 22.00 | 22.00 | 24.00 | 24.00 | 24.00 | 34.00 | 29.00 |
| Shine | | | | | | | |
| Shampoo formulation | +30 | +30 | +35 | +35 | +35 | +28 | +25 |
| Shampoo formulation | | +25 | +25 | +30 | +30 | +28 | +15 |
| Luster | | | | | | | |
| Shampoo/Conditioner composition | +19 | +19 | +20 | +20 | +20 | | |

The examples and comparison examples clearly indicate that adding certain diols and/or esters improve shine and luster in different consumer formulations in synergistic manner.

Examples 33 to 48, Comparative Examples C9 to C12

Tensile Test

Tensile Test refers to a method which measures different linear mechanical properties of the hair fiber. Parameter measured:
  Break extension: maximum extension achieved at breaking point.

Caucasian bleached tresses were treated 5 times with the samples. The tresses were dried at controlled temperature- and humidity (22° C.+/−2° C. and 55% RH) overnight before evaluation. Comparisons among the samples were made. Statistical analysis was performed with analysis of variance, followed by post-test of Tukey, considering 95% of confidence interval. The blends were incorporated at specific concentrations in shampoo and conditioner formulations: example 1=0.1% b.w. in shampoo and 0.5% b.w. in conditioner; example 2=1.0% b.w. in shampoo and 1.0% b.w. in conditioner. Pure ingredients were incorporated at half of its respective blend, i.e.: SymMollient S=0.05% b.w. in shampoo and 0.25% b.w. in conditioner; Biobranil Oily=0.05% b.w. in shampoo and 0.25% b.w. in conditioner; Hydrolite 5=0.5% b.w. in shampoo and 0.5% b.w. in conditioner; and finally Biobranil PGW=0.5% b.w. in shampoo and 0.5% b.w. in conditioner The results are compiled in Table 3a to 3c. Examples 33 to 48 are according to the invention, examples C9 to C12 serve for comparison. The values express the percentage of improvement when compared to placebo.

TABLE 3a

Results tensile test (amounts in % b.w.)

| Compounds | C9 | C10 | C11 | C12 | 33 | 34 |
|---|---|---|---|---|---|---|
| Wheat bran extracts Biobranil ® Oily | 100.00 | — | — | — | 39.45 | — |
| Wheat bran extracts Biobranil ® PGW | — | 100.00 | — | — | — | 10.00 |
| Cetearyl Nonanoate Symmollient ® S | — | — | 100.00 | — | 39.45 | — |
| 1,2-Pentanediol Hydrolite ® 5 | — | — | — | 100.00 | — | 50.00 |
| 1,2-Hexanediol/1,2-Octanediol Symdiol ® 68 | — | — | — | — | — | 1.00 |
| 2-Octyl 3,5,5-trimethyl hexanoate Dragoxat ® 89 | — | — | — | — | 20.00 | — |
| Camillia Olifeira Seed Oil | — | — | — | — | 1.00 | — |
| Alpha-Tocopherol | — | — | — | — | 0.10 | — |
| Glycerol | — | — | — | — | — | 10.00 |
| Water | — | — | — | — | — | 29.00 |
| Break extension | | | | | | |
| Shampoo formulation | +1 | +1 | +3 | +2 | +10 | +7 |
| Shampoo/Conditioner composition | | | | | +1 | +8 |

TABLE 3b

Results tensile test (amounts in % b.w.)

| Compounds | 35 | 36 | 37 | 38 | 39 | 40 | 41 |
|---|---|---|---|---|---|---|---|
| Wheat bran extracts Biobranil ® Oily | 39.45 | — | — | — | 39.45 | — | — |
| Wheat bran extracts Biobranil ® PGW | — | 10.00 | — | — | — | 10.00 | — |
| Protein 1 | — | — | 39.45 | 35.00 | — | — | 20 |
| Protein 2 | — | — | — | 10.00 | — | — | 10.00 |
| Amino acid 1 | — | — | — | — | 1.00 | 1.00 | 1.00 |
| Amino acid 2 | — | — | — | 1.00 | — | 1.00 | 1.00 |
| Cetearyl Nonanoate Symmollient ® S | 39.45 | — | — | 35.50 | 39.45 | — | 15.00 |
| 1,2-Pentanediol Hydrolite ® 5 | — | 40.00 | 15.55 | — | — | 50.00 | 5.00 |
| 1,2-Hexanediol/1,2-Octanediol Symdiol ® 68 | 20.00 | — | 5.00 | — | 19.00 | 1.00 | 10.00 |
| 2-Octyl 3,5,5-trimethyl hexanoate Dragoxat ® 89 | — | 10.00 | — | 17.00 | — | — | — |
| Camillia Olifeira Seed Oil | 1.00 | — | — | 1.00 | 1.00 | — | 0.50 |
| Alpha-Tocopherol | 0.10 | — | — | 0.50 | 0.10 | — | 0.50 |
| Glycerol | — | 10.00 | 10.00 | — | — | 10.00 | 10.00 |
| Water | — | 30.00 | 30.00 | — | — | 27.00 | 27.00 |
| Break extension | | | | | | | |
| Shampoo formulation | +4 | +4 | +10 | +8 | | +10 | |
| Shampoo/Conditioner composition | | | +8 | +7 | +7 | | |

TABLE 3c

Results tensile test (amounts in % b.w.)

| Compounds | 42 | 43 | 44 | 45 | 46 | 47 | 48 |
|---|---|---|---|---|---|---|---|
| Wheat bran extracts Biobranil ® Oily | 29.45 | — | 29.00 | 29.00 | — | — | — |
| Wheat bran extracts Biobranil ® PGW | — | 29.45 | — | — | 29.00 | — | — |
| Keratin | 10.00 | — | 10.00 | 5.00 | 5.00 | 25.00 | — |
| Silk | — | 10.00 | — | 5.00 | 5.00 | — | — |
| l-Arginine | — | — | 1.00 | — | — | 0.50 | 2.50 |
| Glutamic acid | — | — | — | — | 0.50 | 0.50 | 2.50 |
| Tyrosine | — | — | — | 0.50 | — | 0.50 | 2.50 |
| Cysteine | — | — | — | 0.50 | 0.50 | 0.50 | 2.50 |

TABLE 3c-continued

| Compounds | 42 | 43 | 44 | 45 | 46 | 47 | 48 |
|---|---|---|---|---|---|---|---|
| Results tensile test (amounts in % b.w.) | | | | | | | |
| Cetearyl Nonanoate Symmollient ® S | 25.45 | 25.45 | 10.00 | 10.00 | 10.00 | 13.00 | 20.00 |
| 1,2-Pentandiol Hydrolite ® 5 | — | — | 10.00 | 10.00 | 10.00 | 10.00 | 20.00 |
| 1,2-Hexanediol/1,2-Octanediol Symdiol ® 68 | 2.00 | 2.00 | 5.00 | 5.00 | 5.00 | 5.00 | 10.00 |
| 2-Octyl 3,5,5-trimethyl hexanoate Dragoxat ® 89 | — | — | 5.00 | 5.00 | 5.00 | 5.00 | — |
| Camillia Olifeira Seed Oil | 1.00 | 1.00 | 0.50 | 0.50 | 0.50 | 0.50 | 0.50 |
| Alpha-Tocopherol | 0.10 | 0.10 | 0.50 | 0.50 | 0.50 | 0.50 | 0.50 |
| Glycerol | 10.00 | 10.00 | 5.00 | 5.00 | 5.00 | 5.00 | 10.00 |
| Water | 22.00 | 22.00 | 24.00 | 24.00 | 24.00 | 34.00 | 29.00 |
| Break extension | | | | | | | |
| Shampoo formulation | +6 | +6 | +10 | +10 | +10 | +5 | +5 |
| Shampoo/Conditioner composition | | | +10 | +8 | +8 | | |

The examples and comparison examples clearly indicate that adding certain diols and/or esters improve break extension of human hair in different consumer formulations in synergistic manner.

Examples 49 to 64, Comparative Examples C13 to C16

Volume/Frizz Control Assessment

Volume is the gain of body in a hair tress due to its humidity exposure or mechanical actions such as combing or friction of fibers. Frizz is the bristling of some fibers of hair that get apart from the tress body (fly-away effect). Anti-frizz/volume test measures the variation in the shape of the tress after exposure to a high humidity environment, for a controlled period of time. The parameter measured is:

Number of Pixels in the Image

Afro virgin tresses were treated 5 times with the samples and dried at controlled temperature and humidity (22° C.+/−2° C. and 55% RH) overnight before evaluation. They were straightened with a flat iron. Images at initial time were captured. Tresses were left for 4 h at 70% relative humidity environment. Images at final time were captured. Comparisons between initial and final time were made. Statistical analysis was performed with analysis of variance, followed by post-test of Tukey, considering 95% of confidence interval. The blends were incorporated at specific concentrations in shampoo and conditioner formulations: example 1=0.1% b.w. in shampoo and 0.5% b.w. in conditioner; example 2=1.0% b.w. in shampoo and 1.0% b.w. in conditioner. Pure ingredients were incorporated at half of its respective blend, i.e.: SymMollient S=0.05% b.w. in shampoo and 0.25% b.w. in conditioner; Biobranil Oily=0.05% b.w. in shampoo and 0.25% b.w. in conditioner; Hydrolite 5=0.5% b.w. in shampoo and 0.5% b.w. in conditioner; and finally Biobranil PGW=0.5% b.w. in shampoo and 0.5% b.w. in conditioner The results are compiled in Table 4a to 4c. Examples 49 to 64 are according to the invention, examples C13 to C16 serve for comparison. The values express the percentage of improvement when compared to placebo.

TABLE 4a

| Compounds | C13 | C14 | C15 | C16 | 49 | 50 |
|---|---|---|---|---|---|---|
| Results volume/frizz control assessment (amounts in % b.w.) | | | | | | |
| Wheat bran extracts Biobranil ® Oily | 100.00 | — | — | — | 39.45 | — |
| Wheat bran extracts Biobranil ® PGW | — | 100.00 | — | — | — | 10.00 |
| Cetearyl Nonanoate Symmollient ® S | — | — | 100.00 | — | 39.45 | — |
| 1,2-Pentandiol Hydrolite ® 5 | — | — | — | 100.00 | — | 50.00 |
| 1,2-Hexanediol/1,2-Octanediol Symdiol ® 68 | — | — | — | — | — | 1.00 |
| 2-Octyl 3,5,5-trimethyl hexanoate Dragoxat ® 89 | — | — | — | — | 20.00 | — |
| Camillia Olifeira Seed Oil | — | — | — | — | 1.00 | — |
| Alpha-Tocopherol | — | — | — | — | 0.10 | — |
| Glycerol | — | — | — | — | — | 10.00 |
| Water | — | — | — | — | — | 29.00 |
| Volume/Frizz | | | | | | |
| Shampoo formulation | +6 | +5 | +1 | +1 | +16 | +10 |
| Shampoo/Conditioner composition | | | | | +10 | +8 |

TABLE 4b

Results volume/frizz control assessment (amounts in % b.w.)

| Compounds | 51 | 52 | 53 | 54 | 55 | 56 | 57 |
|---|---|---|---|---|---|---|---|
| Wheat bran extracts Biobranil ® Oily | 39.45 | — | — | — | 39.45 | — | — |
| Wheat bran extracts Biobranil ® PGW | — | 10.00 | — | — | — | 10.00 | — |
| Protein 1 | — | — | 39.45 | 35.00 | — | — | 20.00 |
| Protein 2 | — | — | — | 10.00 | — | — | 10.00 |
| Amino acid 1 | — | — | — | — | 1.00 | 1.00 | 1.00 |
| Amino acid 2 | — | — | — | 1.00 | — | 1.00 | 1.00 |
| Cetearyl Nonanoate Symmollient ® S | 39.45 | — | — | 35.50 | 39.45 | — | 15.00 |
| 1,2-Pentandiol Hydrolite ® 5 | — | 40.00 | 15.55 | — | — | 50.00 | 5.00 |
| 1,2-Hexanediol/1,2-Octanediol Symdiol ® 68 | 20.00 | — | 5.00 | — | 19.00 | 1.00 | 10.00 |
| 2-Octyl 3,5,5-trimethyl hexanoate Dragoxat ® 89 | — | 10.00 | — | 17.00 | — | — | — |
| Camillia Olifeira Seed Oil | 1.00 | — | — | 1.00 | 1.00 | — | 0.50 |
| Alpha-Tocopherol | 0.10 | — | — | 0.50 | 0.10 | — | 0.50 |
| Glycerol | — | 10.00 | 10.00 | — | — | 10.00 | 10.00 |
| Water | — | 30.00 | 30.00 | — | — | 27.00 | 27.00 |
| Volume/Frizz | | | | | | | |
| Shampoo formulation | +4 | +4 | +10 | +10 | +10 | | +10 |
| Shampoo/Conditioner composition | | | +8 | +5 | +5 | | |

TABLE 4c

Results volume/frizz control assessment (amounts in % b.w.)

| Compounds | 58 | 59 | 60 | 61 | 62 | 63 | 64 |
|---|---|---|---|---|---|---|---|
| Wheat bran extracts Biobranil ® Oily | 29.45 | — | 29.00 | 29.00 | — | — | — |
| Wheat bran extracts Biobranil ® PGW | — | 29.45 | — | — | 29.00 | — | — |
| Keratin | 10.00 | — | 10.00 | 5.00 | 5.00 | 25.00 | — |
| Silk | — | 10.00 | — | 5.00 | 5.00 | — | — |
| l-Arginine | — | — | 1.00 | — | — | 0.50 | 2.50 |
| Glutamic acid | — | — | — | — | 0.50 | 0.50 | 2.50 |
| Tyrosine | — | — | — | 0.50 | — | 0.50 | 2.50 |
| Cysteine | — | — | — | 0.50 | 0.50 | 0.50 | 2.50 |
| Cetearyl Nonanoate Symmollient ® S | 25.45 | 25.45 | 10.00 | 10.00 | 10.00 | 13.00 | 20.00 |
| 1,2-Pentandiol Hydrolite ® 5 | — | — | 10.00 | 10.00 | 10.00 | 10.00 | 20.00 |
| 1,2-Hexanediol/1,2-Octanediol Symdiol ® 68 | 2.00 | 2.00 | 5.00 | 5.00 | 5.00 | 5.00 | 10.00 |
| 2-Octyl 3,5,5-trimethyl hexanoate Dragoxat ® 89 | — | — | 5.00 | 5.00 | 5.00 | 5.00 | — |
| Camillia Olifeira Seed Oil | 1.00 | 1.00 | 0.50 | 0.50 | 0.50 | 0.50 | 0.50 |
| Alpha-Tocopherol | 0.10 | 0.10 | 0.50 | 0.50 | 0.50 | 0.50 | 0.50 |
| Glycerol | 10.00 | 10.00 | 5.00 | 5.00 | 5.00 | 5.00 | 10.00 |
| Water | 22.00 | 22.00 | 24.00 | 24.00 | 24.00 | 34.00 | 29.00 |
| Volume/Frizz | | | | | | | |
| Shampoo formulation | +8 | +8 | +10 | +10 | +10 | | |
| Shampoo/Conditioner composition | | | +8 | +8 | +8 | | |

The examples and comparison examples clearly indicate that adding certain diols and/or esters improve volume of human hair in different consumer formulations in synergistic manner.

Examples 65 to 80, Comparative Examples C17 to C20 Fluorescence Microscopy

Rhodamine B is cationic and presents affinity with damaged regions of the hair. Tresses are treated and then soaked in solution with Rhodamine B. It reacts with the negative sites of damaged hair. A fluorescent complex is formed in the hair fiber and can be detected when exposed to a fluorescence microscope. After capturing images in the microscope, the intensity of luminance in the images is quantified by image analysis.

The parameter measured is luminance intensity as expression of damage. A treatment that generates images less fluorescents expresses the effect of penetration of the formulation. Caucasian bleached tresses were treated 5 times with the samples. The tresses were dried at controlled temperature and humidity (22° C.+/−2° C. and 55% RH) overnight before evaluation. Microscopic images were made and then analyzed to calculate the luminance intensity. Comparisons between treated and untreated hair were made. Statistical analysis was performed with analysis of variance, followed by post-test of Tukey, considering 95% of confidence interval. The blends were incorporated at specific concentrations in shampoo and conditioner formulations: example 1=0.1% b.w. in shampoo and 0.5% b.w. in conditioner; example 2=1.0% b.w. in shampoo and 1.0% b.w. in conditioner. Pure ingredients were incorporated at half of its respective blend, i.e.: SymMollient S=0.05% b.w. in shampoo and 0.25% b.w. in conditioner; Biobranil Oily=0.05% b.w. in shampoo and 0.25% b.w. in conditioner; Hydrolite 5=0.5% b.w. in shampoo and 0.5% b.w. in conditioner; and finally Biobranil PGW=0.5% b.w. in shampoo and 0.5% b.w. in conditioner. The results are compiled in Table 5a to 5c. Examples 65 to 80 are according to the invention, examples C17 to C20 serve for comparison. The values express the percentage of improvement when compared to untreated hair.

TABLE 5a

Results microscopy (amounts in % b.w.)

| Compounds | C17 | C18 | C19 | C20 | 65 | 66 |
|---|---|---|---|---|---|---|
| Wheat bran extracts Biobranil ® Oily | 100.00 | — | — | — | 39.45 | — |
| Wheat bran extracts Biobranil ® PGW | — | 100.00 | — | — | — | 10.00 |
| Cetearyl Nonanoate Symmollient ® S | — | — | 100.00 | — | 39.45 | — |
| 1,2-Pentanediol Hydrolite ® 5 | — | — | — | 100.00 | — | 50.00 |
| 1,2-Hexanediol/1,2-Octanediol Symdiol ® 68 | — | — | — | — | — | 1.00 |
| 2-Octyl 3,5,5-trimethyl hexanoate Dragoxat ® 89 | — | — | — | — | 20.00 | — |
| Camillia Olifeira Seed Oil | — | — | — | — | 1.00 | — |
| Alpha-Tocopherol | — | — | — | — | 0.10 | — |
| Glycerol | — | — | — | — | — | 10.00 |
| Water | — | — | — | — | — | 29.00 |
| Number of pixels | | | | | | |
| Shampoo formulation | +14 | +11 | +4 | +6 | +30 | +25 |
| Shampoo/Conditioner composition | | | | | +26 | +23 |

TABLE 5b

Results microscopy (amounts in % b.w.)

| Compounds | 67 | 68 | 69 | 70 | 71 | 72 | 73 |
|---|---|---|---|---|---|---|---|
| Wheat bran extracts Biobranil ® Oily | 39.45 | — | — | — | 39.45 | — | — |
| Wheat bran extracts Biobranil ® PGW | — | 10.00 | — | — | — | 10.00 | — |
| Protein 1 | — | — | 39.45 | 35.00 | — | — | 20.00 |
| Protein 2 | — | — | — | 10.00 | — | — | 10.00 |
| Amino acid 1 | — | — | — | — | 1.00 | 1.00 | 1.00 |
| Amino acid 2 | — | — | — | 1.00 | — | 1.00 | 1.00 |
| Cetearyl Nonanoate Symmollient ® S | 39.45 | — | — | 35.50 | 39.45 | — | 15.00 |
| 1,2-Pentanediol Hydrolite ® 5 | — | 40.00 | 15.55 | — | — | 50.00 | 5.00 |
| 1,2-Hexanediol/1,2-Octanediol Symdiol ® 68 | 20.00 | — | 5.00 | — | 19.00 | 1.00 | 10.00 |
| 2-Octyl 3,5,5-trimethyl hexanoate Dragoxat ® 89 | — | 10.00 | — | 17.00 | — | — | — |
| Camillia Olifeira Seed Oil | 1.00 | — | — | 1.00 | 1.00 | — | 0.50 |
| Alpha-Tocopherol | 0.10 | — | — | 0.50 | 0.10 | — | 0.50 |

TABLE 5b-continued

Results microscopy (amounts in % b.w.)

| Compounds | 67 | 68 | 69 | 70 | 71 | 72 | 73 |
|---|---|---|---|---|---|---|---|
| Glycerol | — | 10.00 | 10.00 | — | — | 10.00 | 10.00 |
| Water | — | 30.00 | 30.00 | — | — | 27.00 | 27.00 |
| Number of pixels | | | | | | | |
| Shampoo formulation Shampoo/Conditioner composition | +10 | +15 | +20 | +20 | +20 | +18 | +18 |

TABLE 5c

Results microscopy (amounts in % b.w.)

| Compounds | 74 | 75 | 76 | 77 | 78 | 79 | 80 |
|---|---|---|---|---|---|---|---|
| Wheat bran extracts Biobranil ® Oily | 29.45 | — | 29.00 | 29.00 | — | — | — |
| Wheat bran extracts Biobranil ® PGW | — | 29.45 | — | — | 29.00 | — | — |
| Keratin | 10.00 | — | 10.00 | 5.00 | 5.00 | 25.00 | — |
| Silk | — | 10.00 | — | 5.00 | 5.00 | — | — |
| l-Arginine | — | — | 1.00 | — | — | 0.50 | 2.50 |
| Glutamic acid | — | — | — | — | 0.50 | 0.50 | 2.50 |
| Tyrosine | — | — | — | 0.50 | — | 0.50 | 2.50 |
| Cysteine | — | — | — | 0.50 | 0.50 | 0.50 | 2.50 |
| Cetearyl Nonanoate Symmollient ® S | 25.45 | 25.45 | 10.00 | 10.00 | 10.00 | 13.00 | 20.00 |
| 1,2-Pentandiol Hydrolite ® 5 | — | — | 10.00 | 10.00 | 10.00 | 10.00 | 20.00 |
| 1,2-Hexanediol/1,2-Octanediol Symdiol ® 68 | 2.00 | 2.00 | 5.00 | 5.00 | 5.00 | 5.00 | 10.00 |
| 2-Octyl 3,5,5-trimethyl hexanoate Dragoxat ® 89 | — | — | 5.00 | 5.00 | 5.00 | 5.00 | — |
| Camillia Olifeira Seed Oil | 1.00 | 1.00 | 0.50 | 0.50 | 0.50 | 0.50 | 0.50 |
| Alpha-Tocopherol | 0.10 | 0.10 | 0.50 | 0.50 | 0.50 | 0.50 | 0.50 |
| Glycerol | 10.00 | 10.00 | 5.00 | 5.00 | 5.00 | 5.00 | 10.00 |
| Water | 22.00 | 22.00 | 24.00 | 24.00 | 24.00 | 34.00 | 29.00 |
| Number of pixels | | | | | | | |
| Shampoo formulation Shampoo/Conditioner composition | +10 | +30 | +12 | +15 | +33 | +18 | +18 |

The examples and comparison examples clearly indicate that adding certain diols and/or esters reduces damage of human hair in different consumer formulations in synergistic manner.

Examples 81 to 97, Comparative Examples C21 to C24

Swelling Test

Through diameter measurements, it is possible to determine the level of swelling of a fiber of hair over time. The laser measures the variation in the fiber diameter as it absorbs water over a pre-determined time. According to the fiber condition or the film covering its surface, the level of swelling may change. The more damaged the hair, more hydrophilic it is and, consequently, more swelling is noticed since most of the hair damages take the lipids, ceramides and other hydrophobic substances away from the hair. The parameter measured is:

% of swelling as % of the fiber diameter variation.

Caucasian bleached tresses were treated 5 times with the samples. The tresses were dried at controlled temperature and humidity (22° C.+/−2° C. and 55% RH) overnight before evaluation. Comparisons among the samples were made. Statistical analysis was performed with analysis of variance, followed by post-test of Tukey, considering 95% of confidence interval. The blends were incorporated at specific concentrations in shampoo and conditioner formulations: example 1=0.1% b.w. in shampoo and 0.5% b.w. in conditioner; example 2=1.0% b.w. in shampoo and 1.0% b.w. in conditioner. Pure ingredients were incorporated at half of its respective blend, i.e.: SymMollient S=0.05% b.w. in shampoo and 0.25% b.w. in conditioner; Biobranil Oily=0.05% b.w. in shampoo and 0.25% b.w. in conditioner; Hydrolite 5=0.5% b.w. in shampoo and 0.5% b.w. in conditioner; and finally Biobranil PGW=0.5% b.w. in shampoo and 0.5% b.w. in conditioner. The results are compiled in Table 6a to 6c. Examples 81 to 97 are according to the invention, examples C21 to C24 serve for comparison. The values express the percentage of improvement when compared to untreated hair.

TABLE 6a

Results swelling test (amounts in % b.w.)

| Compounds | C21 | C22 | C23 | C24 | 81 | 82 |
|---|---|---|---|---|---|---|
| Wheat bran extracts Biobranil ® Oily | 100.00 | — | — | — | 39.45 | — |
| Wheat bran extracts Biobranil ® PGW | — | 100.00 | — | — | — | 10.00 |
| Cetearyl Nonanoate Symmollient ® S | — | — | 100.00 | — | 39.45 | — |
| 1,2-Pentanediol Hydrolite ® 5 | — | — | — | 100.00 | — | 50.00 |
| 1,2-Hexanediol/1,2-Octanediol Symdiol ® 68 | — | — | — | — | — | 1.00 |
| 2-Octyl 3,5,5-trimethyl hexanoate Dragoxat ® 89 | — | — | — | — | 20.00 | — |
| Camillia Olifeira Seed Oil | — | — | — | — | 1.00 | — |
| Alpha-Tocopherol | — | — | — | — | 0.10 | — |
| Glycerol | — | — | — | — | — | 10.00 |
| Water | — | — | — | — | — | 29.00 |
| Shape retention | | | | | | |
| Shampoo formulation | +15 | +11 | +4 | +3 | +36 | +31 |
| Shampoo/Conditioner composition | | | | | +30 | +25 |

TABLE 6b

Results swelling test (amounts in % b.w.)

| Compounds | 83 | 84 | 85 | 86 | 87 | 88 | 89 |
|---|---|---|---|---|---|---|---|
| Wheat bran extracts Biobranil ® Oily | 39.45 | — | — | — | 39.45 | — | — |
| Wheat bran extracts Biobranil ® PGW | — | 10.00 | — | — | — | 10.00 | — |
| Protein 1 | — | 39.45 | 35.00 | — | — | 20.00 | — |
| Protein 2 | — | — | — | 10.00 | — | — | 10.00 |
| Amino acid 1 | — | — | — | — | 1.00 | 1.00 | 1.00 |
| Amino acid 2 | — | — | — | 1.00 | — | 1.00 | 1.00 |
| Cetearyl Nonanoate Symmollient ® S | 39.45 | — | — | 35.50 | 39.45 | — | 15.00 |
| 1,2-Pentanediol Hydrolite ® 5 | — | 40.00 | 15.55 | — | — | 50.00 | 5.00 |
| 1,2-Hexanediol/1,2-Octanediol Symdiol ® 68 | 20.00 | — | 5.00 | — | 19.00 | 1.00 | 10.00 |
| 2-Octyl 3,5,5-trimethyl hexanoate Dragoxat ® 89 | — | 10.00 | — | 17.00 | — | — | — |
| Camillia Olifeira Seed Oil | 1.00 | — | — | 1.00 | 1.00 | — | 0.50 |
| Alpha-Tocopherol | 0.10 | — | — | 0.50 | 0.10 | — | 0.50 |
| Glycerol | — | 10.00 | 10.00 | — | — | 10.00 | 10.00 |
| Water | — | 30.00 | 30.00 | — | — | 27.00 | 27.00 |
| Shape retention | | | | | | | |
| Shampoo formulation Shampoo/Conditioner composition | +30 | +20 | +25 | +30 | +30 | +20 | +25 |

TABLE 6c

Results swelling test (amounts in % b.w.)

| Compounds | 90 | 92 | 93 | 94 | 95 | 96 | 97 |
|---|---|---|---|---|---|---|---|
| Wheat bran extracts Biobranil ® Oily | 29.45 | — | 29.00 | 29.00 | — | — | — |
| Wheat bran extracts Biobranil ® PGW | — | 29.45 | — | — | 29.00 | — | — |
| Keratin | 10.00 | — | 10.00 | 5.00 | 5.00 | 25.00 | — |
| Silk | — | 10.00 | — | 5.00 | 5.00 | — | — |
| l-Arginine | — | — | 1.00 | — | — | 0.50 | 2.50 |
| Glutamic acid | — | — | — | — | 0.50 | 0.50 | 2.50 |
| Tyrosine | — | — | — | 0.50 | — | 0.50 | 2.50 |
| Cysteine | — | — | — | 0.50 | 0.50 | 0.50 | 2.50 |

TABLE 6c-continued

Results swelling test (amounts in % b.w.)

| Compounds | 90 | 92 | 93 | 94 | 95 | 96 | 97 |
|---|---|---|---|---|---|---|---|
| Cetearyl Nonanoate Symmollient ® S | 25.45 | 25.45 | 10.00 | 10.00 | 10.00 | 13.00 | 20.00 |
| 1,2-Pentanediol Hydrolite ® 5 | — | — | 10.00 | 10.00 | 10.00 | 10.00 | 20.00 |
| 1,2-Hexanediol/1,2-Octanediol Symdiol ® 68 | 2.00 | 2.00 | 5.00 | 5.00 | 5.00 | 5.00 | 10.00 |
| 2-Octyl 3,5,5-trimethyl hexanoate Dragoxat ® 89 | — | — | 5.00 | 5.00 | 5.00 | 5.00 | — |
| Camillia Olifeira Seed Oil | 1.00 | 1.00 | 0.50 | 0.50 | 0.50 | 0.50 | 0.50 |
| Alpha-Tocopherol | 0.10 | 0.10 | 0.50 | 0.50 | 0.50 | 0.50 | 0.50 |
| Glycerol | 10.00 | 10.00 | 5.00 | 5.00 | 5.00 | 5.00 | 10.00 |
| Water | 22.00 | 22.00 | 24.00 | 24.00 | 24.00 | 34.00 | 29.00 |
| Shape retention | | | | | | | |
| Shampoo formulation Shampoo/Conditioner composition | +28 | +26 | +25 | +30 | +30 | +20 | +20 |

The examples and comparison examples clearly indicate that adding certain diols and/or esters improves shape retention of human hair in different consumer formulations in synergistic manner.

FORMULATION EXAMPLES

TABLE I

Shampoo (Amounts in % b.w.)

| Ingredients | Amount |
|---|---|
| Sodium lauryl ether sulfate (e.g. Texapon NSO) | 12 |
| Cocamidopropyl betaine (e.g. Dehyton K) | 2 |
| Sodium chloride | 1.4 |
| Citric acid | 1.3 |
| Perfume oil P1. P2. P3 or P4 | 0.3 |
| Phenoxyethanol. methyl-. ethyl-. butyl- and propylparaben | 0.5 |
| Mixture according to Example 2 | 2.0 |
| Water | Ad 100 |

TABLE II 2-in-1 Shampoo (Amounts in % b.w.)

| Ingredients | INCI Name | Amount |
|---|---|---|
| Deionized water | Water | Ad 100 |
| Plantacare PS 10 | Sodium Laureth Sulfate. Lauryl Glucoside | 20.0 |
| Euperlan PK 771 | Glycol Distearate. Sodium Lauryl Sulfate. Cocamide MEA. Laureth-10 | 6.0 |
| Sodium chloride | Sodium Chloride | 1.4 |
| Citric acid monohydrate crystalline | Citric acid | 0.1 |
| Perfume oil P1. P2. P3 or P4 | Fragrance | 0.5 |
| Dragocid Liquid | Phenoxyethanol, Parabens | 0.5 |
| Mixture according to Example 2 | | 3.0 |

TABLE III

Anti-dandruff Shampoo (Amounts in % b.w.)

| Ingredients | Amount |
|---|---|
| Climbazole | 0.50 |
| Sodium Laureth Sulfate | 37.00 |
| Cocamidopropyl Betaine | 8.00 |
| PEG-6 Caprylic/Capric Glycerides | 2.50 |
| Laureth-2 | 2.00 |
| Water (Aqua). Glycerol. *Thymus Vulgaris* (Thyme). Flower/Leaf Extract | 0.50 |
| *Rosmarinus Officinalis* (Rosemary) Leaf Water. Water (Aqua). Butylene Glycol. Pentylene Glycol | 0.50 |
| Bisabolol | 0.10 |
| Panthenol | 0.50 |
| Polyquaternium-10 | 0.40 |
| Perfume oil P1. P2. P3 or P4 | 0.50 |
| Phenoxyethanol. Methylparaben. Ethylparaben. Butylparaben. Propylparaben. Isobutylparaben | 0.70 |
| Mixture according to Example 2 | 2.00 |
| Water (Aqua) | Ad 100 |

TABLE IV

Hair conditioner with Crinipan. rinse-off (Amounts in % b.w.)

| Ingredients | INCI Name | Amount |
|---|---|---|
| Lanette ® O | Cetearyl Alcohol | 4.00 |
| Dragoxat 89 | Ethylhexyl Isononanoate | 2.00 |
| Genamin ® KDM-P | Behentrimonium Chloride | 1.00 |
| SF 1550 | Phenyl Trimethicone | 0.10 |
| Neo Heliopan ® BB | Benzophenone-3 | 0.10 |

TABLE IV-continued

Hair conditioner with Crinipan, rinse-off (Amounts in % b.w.)

| Ingredients | INCI Name | Amount |
| --- | --- | --- |
| Crinipan ® AD | Climbazole | 0.80 |
| Glycerol 99.5 P. | Glycerol | 6.00 |
| Water | Water (Aqua) | Ad 100 |
| Actipone ® Alpha Pulp | Water (Aqua). Butylene Glycol. Malic Acid. *Actinidia Chinensis* (Kiwi) Fruit Juice. *Citrus. Aurantium Dulcis* (Orange). Juice. *Citrus Paradisi* (Grapefruit) Juice. *Pyrus Malus* (Apple) Juice. Trideceth-9. *Prunus Amygdalus Dulcis* (Sweet Almond) Seed Extract | 0.50 |
| Extrapone ® Bamboo P | Propylene Glycol. Water (Aqua). Butylene Glycol. *Bambusa Vulgaris* Shoot Extract | 0.50 |
| Sodium Hydroxide 10% solution | Sodium Hydroxide | 0.40 |
| Colour I | Colour | 0.60 |
| Colour II | Colour | 0.30 |
| Perfume oil P1. P2. P3 or P4 | Fragrance | 0.40 |
| Preservative | Methylparaben | 0.20 |
| Mixture according to Example 2 | | 2.00 |

TABLE V

Sprayable hair conditioner with zinc pyrithrione, leave-on (Amounts in % b.w.)

| Ingredients | INCI Name | Amount |
| --- | --- | --- |
| Monomuls 60-35 C | Hydrogenated Palm Glycerides | 1.70 |
| Cetiol OE | Dicaprylyl Ether | 7.20 |
| Abil 100 | Dimethicone | 3.60 |
| Dehyquart F 75 | Distearoylethyl Hydroxyethylmonium. Methosulfate. Cetearyl Alcohol | 4.00 |
| Eumulgin B1 | Ceteareth-12 | 3.50 |
| Cetiol S | Diethylhexylcyclohexane | 7.20 |
| D-Panthenol | Panthenol | 0.10 |
| Glycerol 99.5 P. | Glycerol | 1.50 |
| Water | Water (Aqua) | Ad 100 |
| Actipone ® Rosemary | Water (Aqua). Propylene. Glycol. *Rosmarinus Officinalis.* (Rosemary) Leaf Extract | 0.10 |
| Frescolat ® ML Cryst. | Menthyl Lactate | 0.50 |
| Dragosantol100 | Bisabolol | 0.10 |
| Zinc Omadine | Zinc pyrithione | 0.10 |
| Perfume oil P1. P2. P3 or P4 | Fragrance | 0.40 |
| Phenonip ® | phenoxyethanol. methylparaben. ethylparaben. butylparaben. propylparaben. isobutylparaben | 0.30 |
| Mixture according to Example 2 | | 2.0 |

TABLE VI

Hair conditioner with UV protection (Amounts in % b.w.)

| Ingredients | INCI Name | Amount |
| --- | --- | --- |
| Renex PEG 6000 | PEG-150 | 2.50 |
| Hair Conditioner Base | Cetyl alcohol. behentrimonium chloride. *Triticum Vulgare* (Wheat) bran extract. linoleic acid | 3.00 |
| PCL-Solid | Stearyl heptanoate. stearyl caprylate | 0.50 |
| Dow Corning 5200 | Laurylmethicone copolyol | 0.50 |
| Natrosol 250 HR | Hydroxyethylcellulose | 0.50 |
| Benzophenone-4 | Benzophenone-4 | 1.00 |
| Neo Heliopan AP | Disodiumphenyldibenz-imidazole tetrasulphonate | 1.00 |
| Amino methyl propanol | Amino methyl propanol | 2.00 |
| Dow Corning 949 cationic emulsion | Amodimethicone. cetrimonium chloride. trideceth-12 | 2.00 |
| Perfume oil P1. P2. P3 or P4 | Fragrance | 0.80 |
| 1.2-hexanediol | 1.2-hexanediol | 0.50 |
| Mixture according to Example 1 | | 2.00 |
| Water | Water (Aqua) | Ad 100 |

The invention claimed is:

1. A blend consisting of:
   (a) at least one wheat bran extract, and
   (b1) at least carboxylic acid alkyl ester, and/or
   (b2) at least one diol, and optionally
   (c) at least one auxiliary agent wherein said auxiliary agent(s) (c) is selected from the group consisting of water, ethanol, ethylene glycol, propylene glycol, glycerol, oil bodies, and other lipophilic additives 2. The blend of claim 1, comprising a carboxylic acid ester of general formula (I)

$$R^1COO\text{---}R^2 \qquad (I)$$

in which $R^1CO$ is a saturated or unsaturated, linear or branched acyl radical having 6 to 22 carbon atoms and $R^2$ is a linear or branched alkyl or alkenyl radical having 1 to 22 carbon atoms.

3. The blend of claim 2, comprising a carboxylic acid ester of formula (I) in which $R^1CO$ is a saturated, linear acyl radical having 8 to 12 carbon atoms.

4. The blend of claim 2, comprising a carboxylic acid ester of formula (I) in which $R^2$ is a linear alkyl radical having 12 to 18 carbon atoms.

5. The blend of claim 2, wherein said carboxylic acid ester is cetearyl nonanoate.

6. The blend of claim 1, wherein said diol is a 1,2-alkandiol.

7. The blend of claim 6, comprising an 1,2-alkandiol of general formula (II)

$$R^3\text{—CH(OH)CH}_2\text{OH} \qquad \text{(II)}$$

in which $R^3$ is an alkyl radical having 5 to 12 carbon atoms.

8. The blend of claim 7, wherein said 1,2-alkandiol is selected from the group consisting of 1,2-pentandiol, 1,2-hexandiol, 1,2-octandiol and mixtures thereof.

9. The blend of claim 1, comprising components (a) and (b1+b2) in a ratio by weight of about 1:5 to about 5:1.

10. The blend of claim 1 consisting of
   (a) from about 5 to about 50 wt. percent of said at least one wheat bran extract, and
   (b1) from about 10 to about 70 wt. percent of said at least carboxylic acid alkyl ester, and/or
   (b2) from about 0.1 to about 70 wt. percent of said at least one diol, and optionally
   (c) from about 0.001 to about 20 wt. percent of said at least one auxiliary agent,
     on condition that all of the components add together to 100 wt. percent based on the total weight of the blend.

* * * * *